(12) United States Patent
Duchon et al.

(10) Patent No.: US 11,602,272 B2
(45) Date of Patent: Mar. 14, 2023

(54) OPHTHALMIC OPTICAL COHERENCE TOMOGRAPHY WITH MULTIPLE RESOLUTIONS

(71) Applicant: Alcon Inc., Fribourg (CH)

(72) Inventors: Brent Duchon, Cypress, CA (US); Muhammad K. Al-Qaisi, Ladera Ranch, CA (US); Richard J. Michaels, Irvine, CA (US); Steve X. Chen, San Diego, CA (US)

(73) Assignee: Alcon Inc., Fribourg (CH)

( * ) Notice: Subject to any disclaimer, the term of this patent is extended or adjusted under 35 U.S.C. 154(b) by 376 days.

(21) Appl. No.: 16/876,960

(22) Filed: May 18, 2020

(65) Prior Publication Data

US 2020/0367744 A1 Nov. 26, 2020

Related U.S. Application Data

(60) Provisional application No. 62/850,164, filed on May 20, 2019.

(51) Int. Cl.

| | |
|---|---|
| *G02B 13/22* | (2006.01) |
| *A61B 3/10* | (2006.01) |
| *G01B 9/02015* | (2022.01) |
| *G01B 9/02091* | (2022.01) |
| *G02B 13/06* | (2006.01) |
| *G02B 15/15* | (2006.01) |
| *G02B 27/10* | (2006.01) |

(52) U.S. Cl.
CPC ............ *A61B 3/102* (2013.01); *G01B 9/0203* (2013.01); *G01B 9/02091* (2013.01); *G02B 13/06* (2013.01); *G02B 13/22* (2013.01); *G02B 15/15* (2013.01); *G02B 27/1006* (2013.01)

(58) Field of Classification Search
CPC ........ G02B 13/06; G02B 13/22; G02B 15/15; G02B 27/1006
See application file for complete search history.

(56) References Cited

U.S. PATENT DOCUMENTS

2018/0055355 A1* 3/2018 Sarunic ................ A61B 3/1241

FOREIGN PATENT DOCUMENTS

KR 2015-0043115 A 4/2015

* cited by examiner

Primary Examiner — Joseph P Martinez

(57) ABSTRACT

Systems and methods are disclosed for performing ophthalmic optical coherence tomography with multiple resolutions. In some embodiments, a system comprises a light source, an output lens, and a set of optical components between the light source and the output lens, the set of optical components comprising an afocal zoom telescope. The set of optical components is adapted to provide imaging both at a first field of view with a first resolution and at a second field of view with a second resolution, wherein the first field of view is wider than the second field of view and the second resolution is higher than the first resolution. A method of performing ophthalmic optical coherence tomography with multiple resolutions may be performed using one or more of the systems described herein.

17 Claims, 9 Drawing Sheets

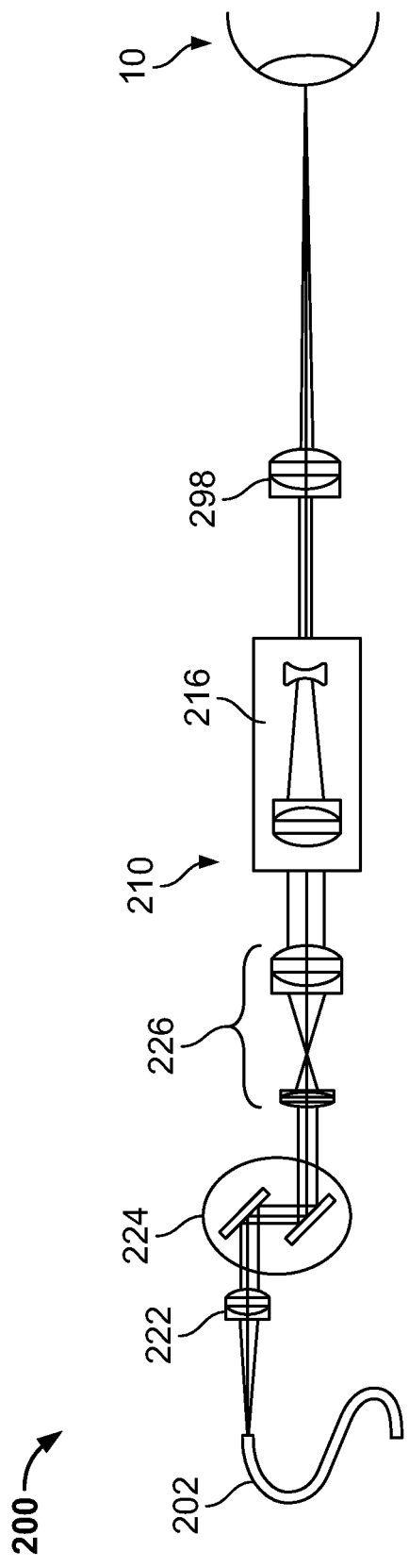
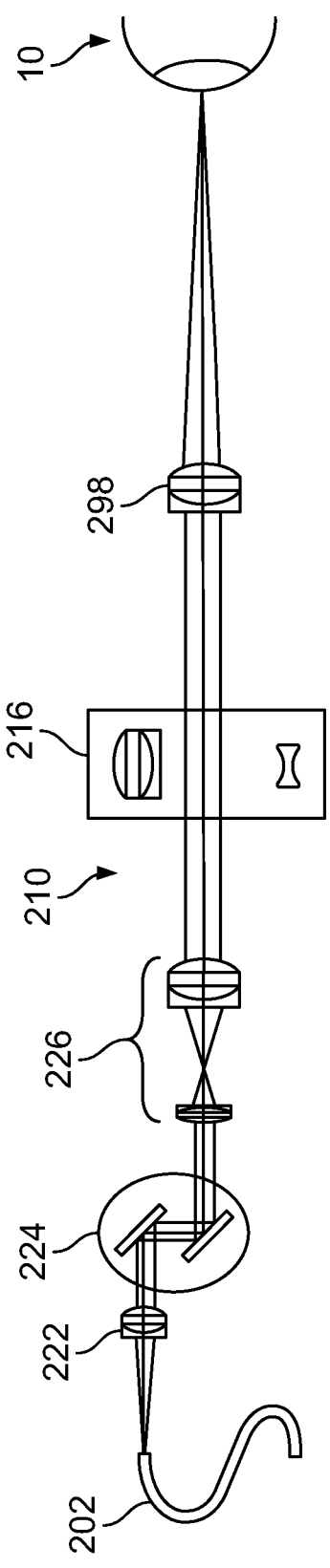
FIG. 2A
FIG. 2B

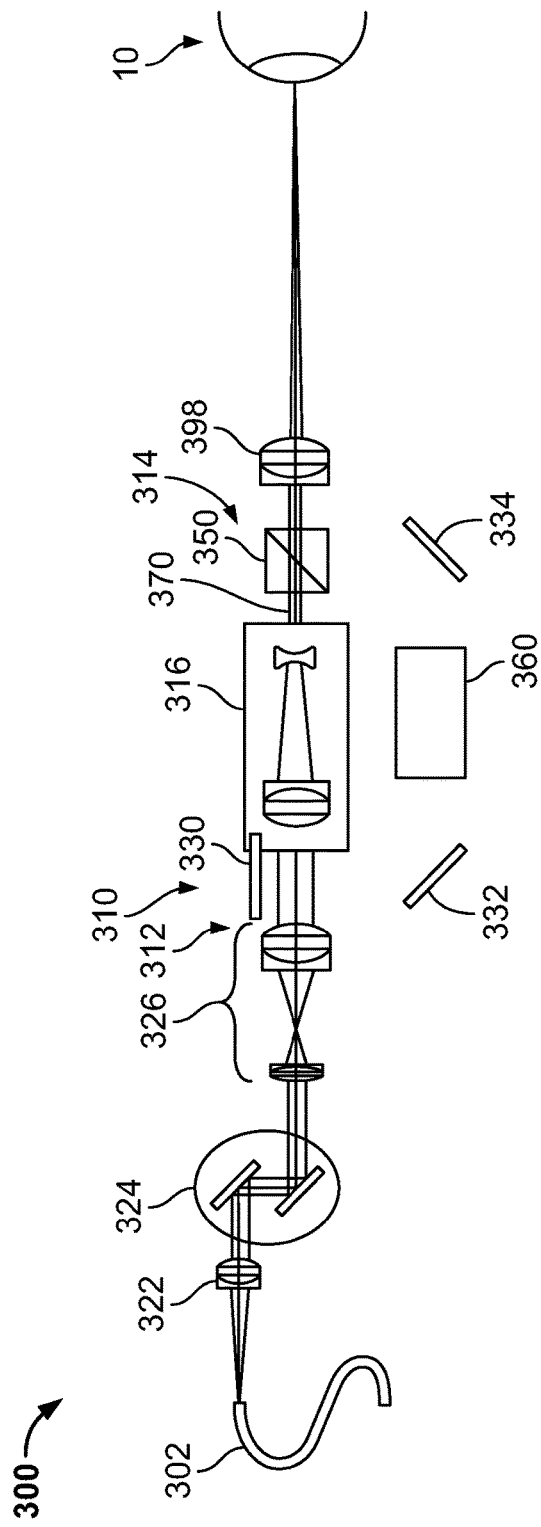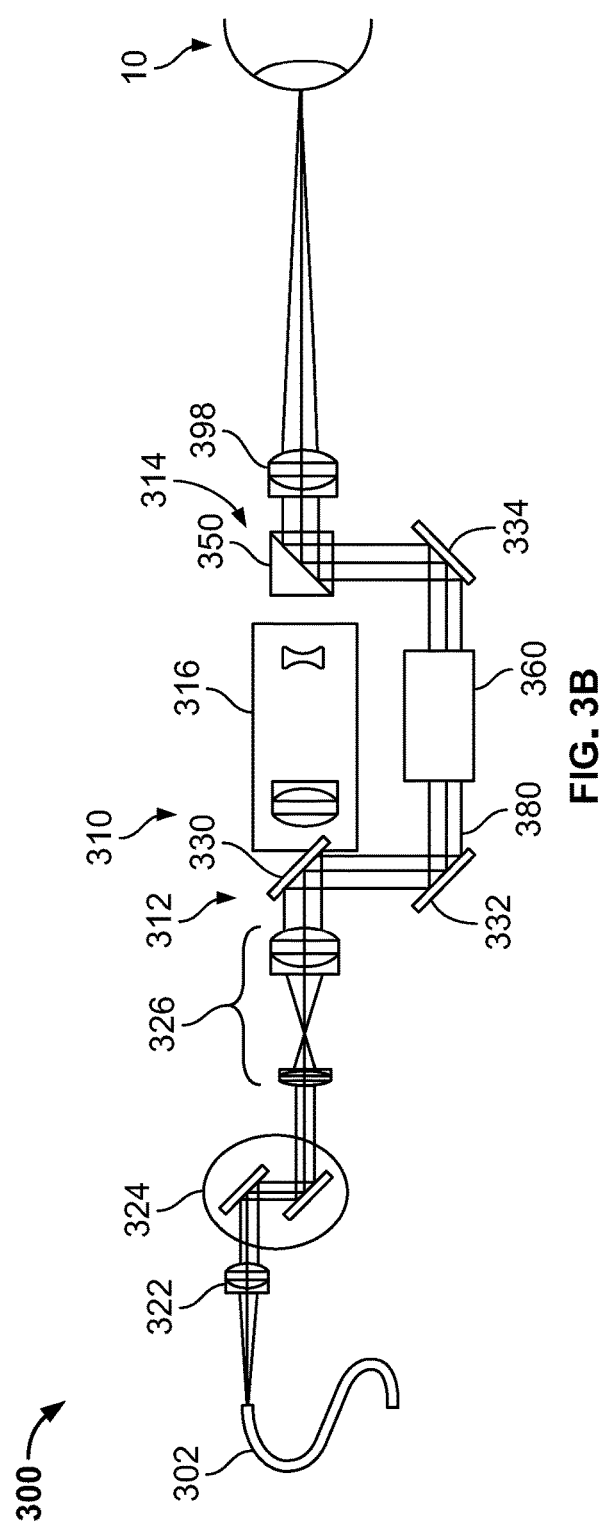

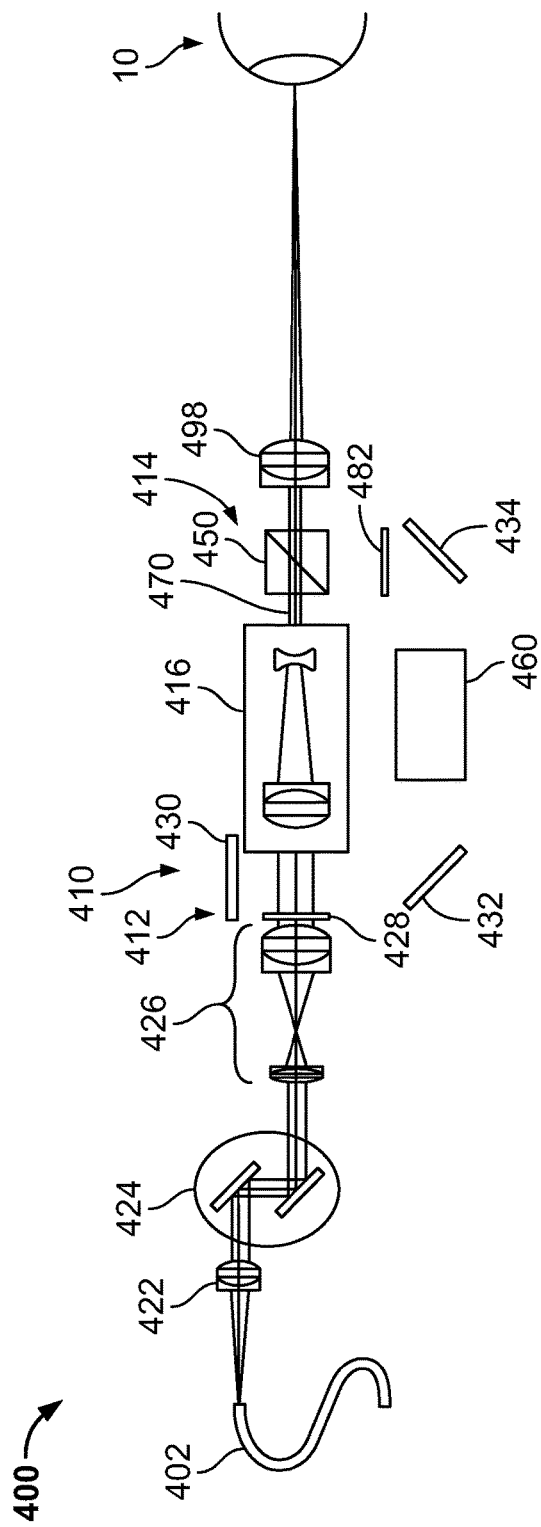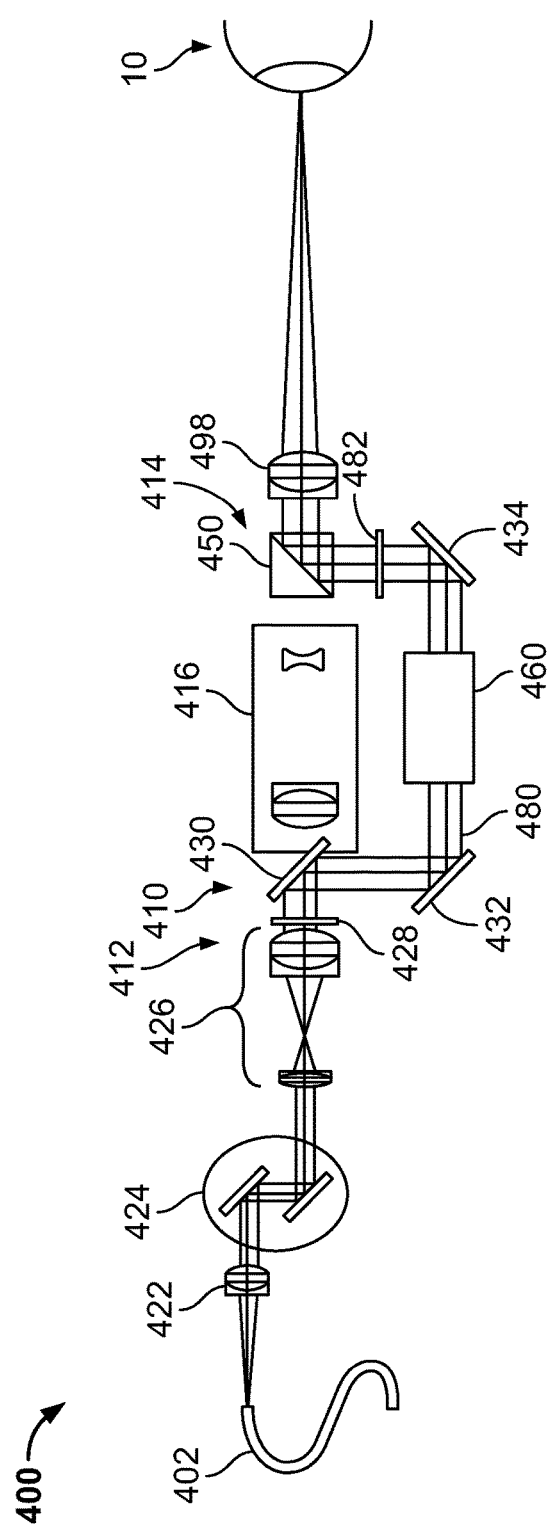

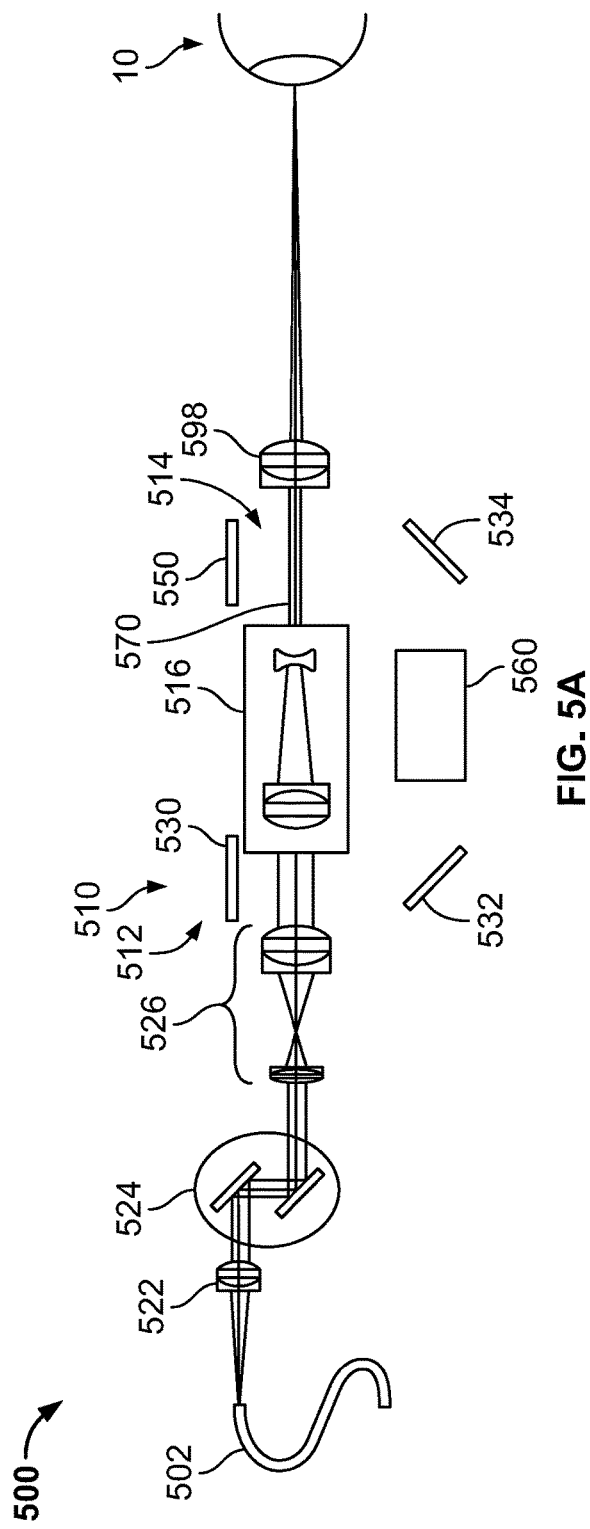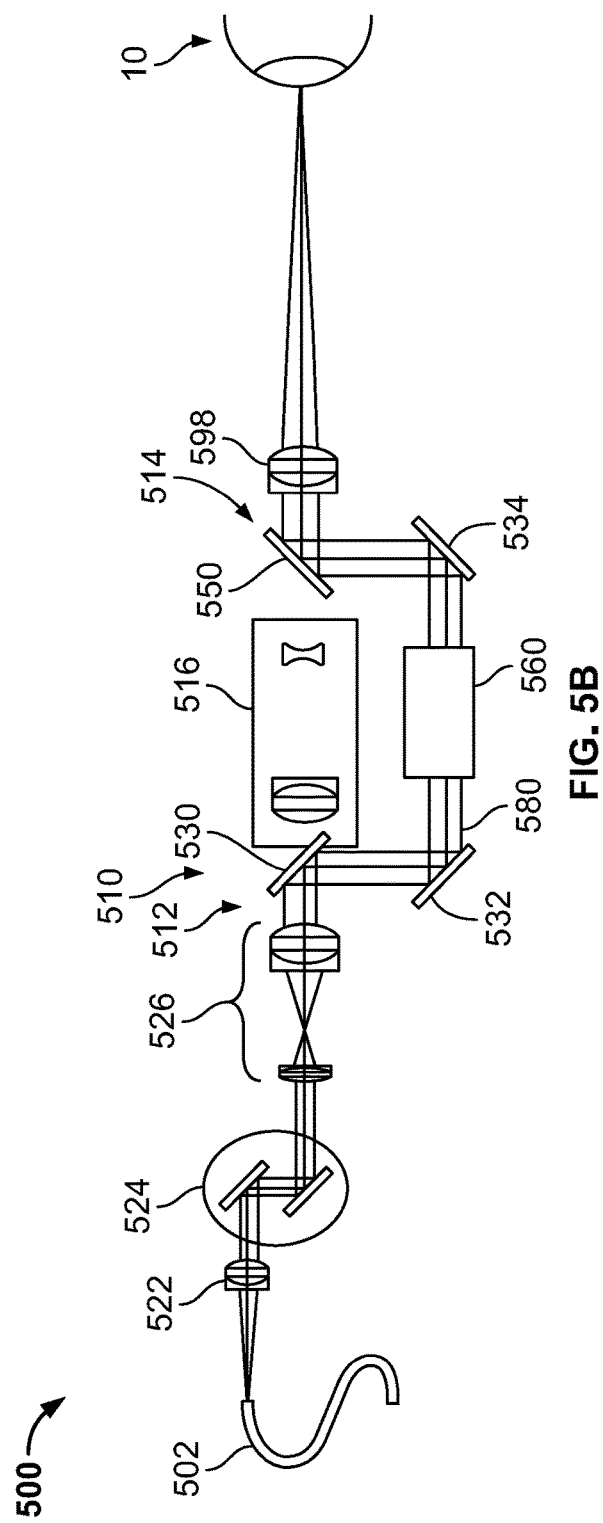

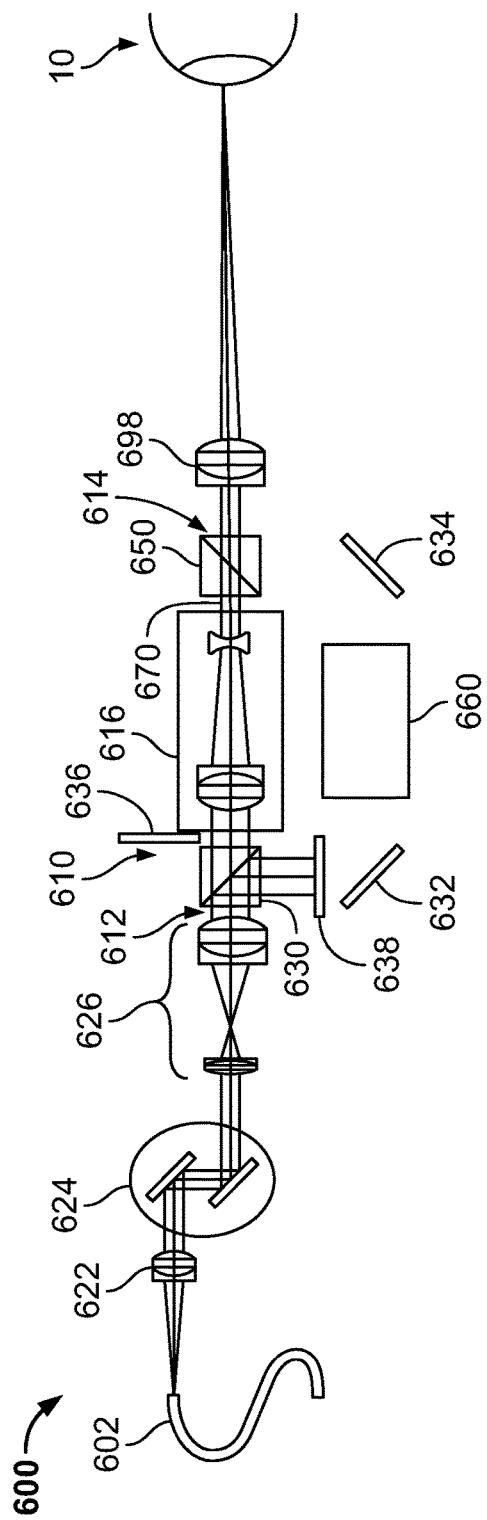
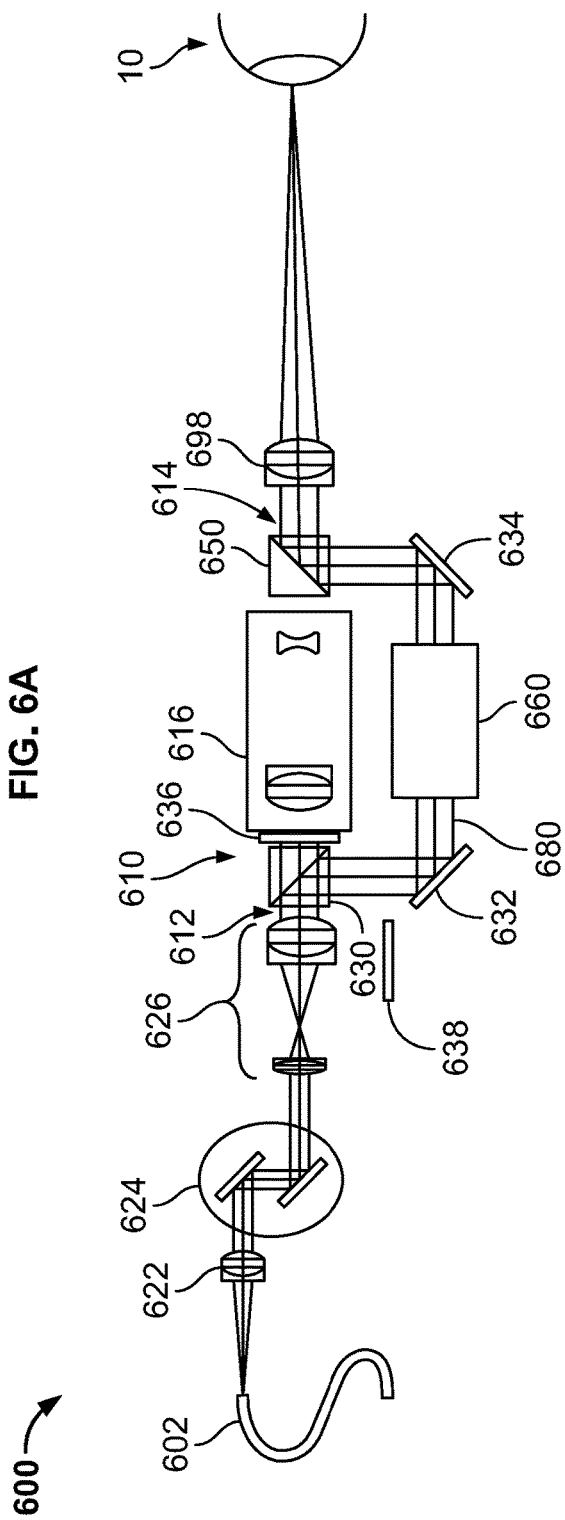
FIG. 6A
FIG. 6B

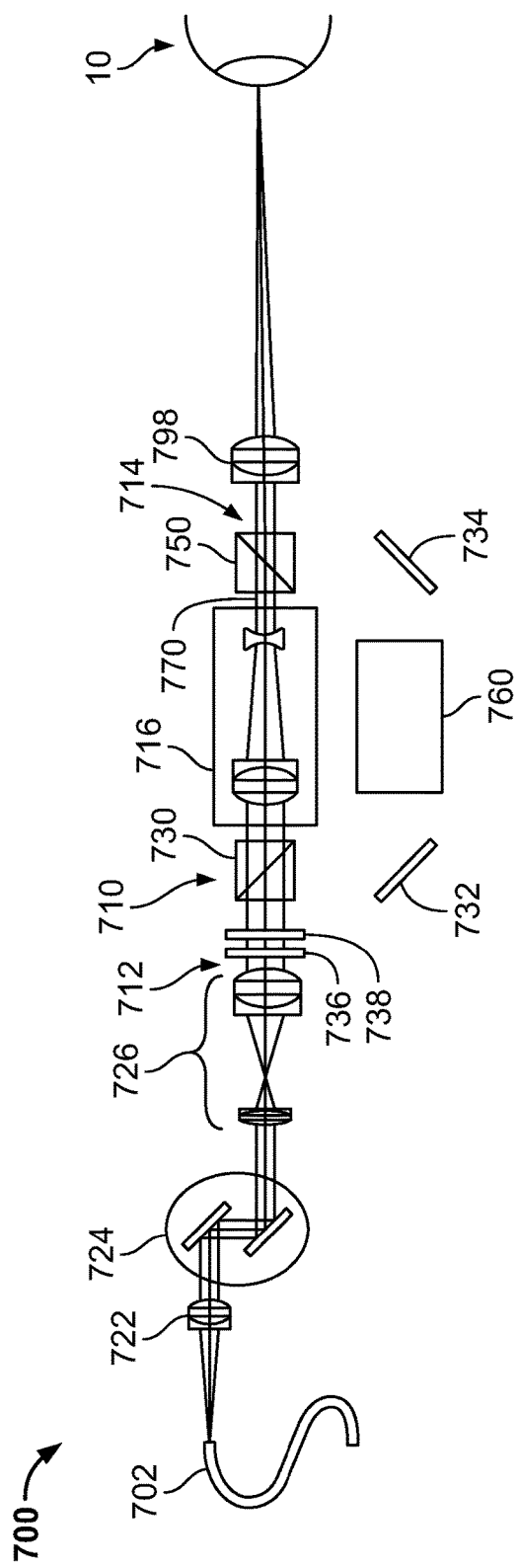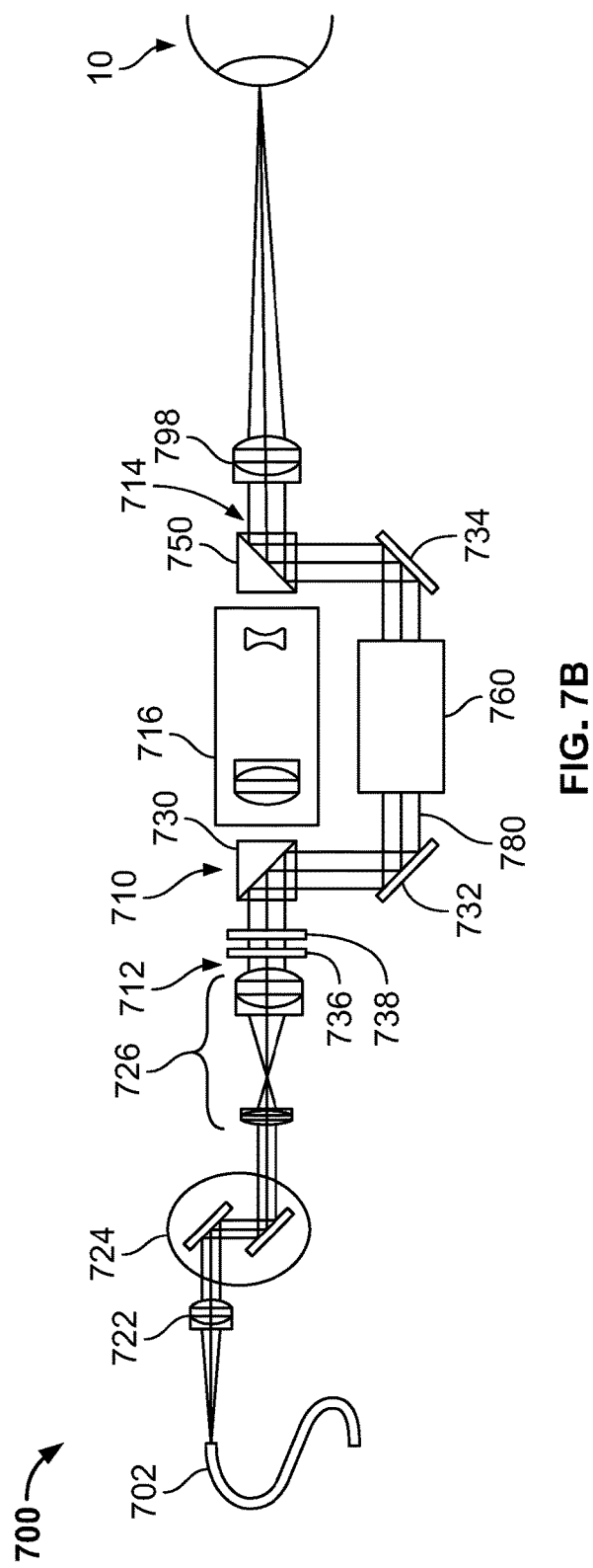

OPHTHALMIC OPTICAL COHERENCE TOMOGRAPHY WITH MULTIPLE RESOLUTIONS

TECHNICAL FIELD

The present disclosure is directed to systems and methods relating to ophthalmic optical coherence tomography.

BACKGROUND

Imaging by optical coherence tomography (OCT) is a widely-used imaging technique for ophthalmic images. OCT is a non-invasive diagnostic procedure that can provide in vivo cross-sectional subsurface imaging across tissue layers. OCT has been used for posterior segment imaging, for example to examine the retina, and for anterior segment imaging, for example to examine the lens and/or cornea. OCT can aid ophthalmologists in diagnosing eye problems, modelling the eye, and providing pre-operative information for surgery.

A need exists for improvements in systems and methods for ophthalmic OCT.

SUMMARY

The present disclosure is directed to systems and methods for performing ophthalmic optical coherence tomography with multiple resolutions.

In some embodiments, a system comprises a light source, an output lens, and a set of optical components between the light source and the output lens, the set of optical components comprising an afocal zoom telescope. The set of optical components is adapted to provide imaging both at a first field of view with a first resolution and at a second field of view with a second resolution, wherein the first field of view is wider than the second field of view and the second resolution is higher than the first resolution. The set of optical components is adapted to provide imaging at least at the first field of view by passing light emitted from the light source through the afocal zoom telescope.

In some embodiments, the set of optical components may have a first configuration providing the first field of view with the first resolution and a second configuration providing the second field of view with the second resolution.

In some embodiments, the afocal zoom telescope comprises a zoom lens, wherein the position of the zoom lens is movable between a first position and a second position, wherein when the zoom lens is in its first position the set of optical components is in its first configuration, and wherein when the zoom lens is in its second position the set of optical components is in its second configuration.

In some embodiments, the afocal zoom telescope is movable between a first position and a second position, wherein when the afocal zoom telescope is in its first position the set of optical components is in its first configuration, and wherein when the afocal zoom telescope is in its second position the set of optical components is in its second configuration. In some embodiments, when the afocal zoom telescope is in its first position, the system is configured such that light emitted from the light source passes through the afocal zoom telescope, and when the afocal zoom telescope is in its second position, the system is configured such that light emitted from the light source does not pass through the afocal zoom telescope. The afocal zoom telescope may be movable by rotation and/or translation of the afocal zoom telescope.

In some embodiments, when the set of optical components is in its first configuration, the system is configured such that light emitted from the light source travels along a first optical path, and when the set of optical components is in its second configuration, the system is configured such that light emitted from the light source travels along a second optical path. The first optical path may be a path that passes through the afocal zoom telescope, and the second optical path may be a path that does not pass through the afocal zoom telescope or that passes through a different afocal zoom telescope.

In some embodiments, the set of optical components may comprise a first mirror at an input end of the set of optical components, wherein the first mirror is movable between a first position and a second position, wherein when the first mirror is in its first position the system is configured such that light emitted from the light source travels along the first optical path, and wherein when the first mirror is in its second position, the system is configured such that light emitted from the light source travels along the second optical path.

In some embodiments, the set of optical components may further comprise polarization optics at an input end of the set of optical components, a polarization rotation device in the second optical path, and a polarizing beam splitter at an output end of the set of optical components.

In some embodiments, the set of optical components may further comprise a second mirror at an output end of the set of optical components.

In some embodiments, the set of optical components may further comprise a beam splitter at an output end of the set of optical components.

In some embodiments, the set of optical components may further comprise a beam splitter, a first shutter, and a second shutter at an input end of the set of optical components, wherein when the set of optical components is in its first configuration, the second shutter prevents light emitted from the light source from traveling through the second optical path, and wherein when the set of optical components is in its second configuration, the first shutter prevents light emitted from the light source from traveling through the first optical path.

In some embodiments, the set of optical components may further comprise a polarization rotation device and a polarizing beam splitter an input end of the set of optical components and a polarizing beam splitter at an output end of the set of optical components.

In some embodiments, the set of optical components may further comprise an input polarizing beam splitter at an input end of the set of optical components, wherein the input polarizing beam splitter is adapted to split incoming light such that light at a first polarization travels along a first optical path that passes through an afocal zoom telescope and such that light at a second polarization travels along a second optical path that does not pass through the afocal zoom telescope. The first polarization may be one of TE or TM polarization and the second polarization may be the other of TE or TM polarization. The set of optical components may further comprise an output polarizing beam splitter at an output end of the set of optical components. The system may further comprise an interferometer with detectors adapted to select each of the first polarization and the second polarization.

In some embodiments, a method of performing ophthalmic optical coherence tomography with multiple resolutions comprises emitting light from a light source, passing light from the light source through a set of optical components at a first field of view with a first resolution, and passing light from the light source through the set of optical components at a second field of view with a second resolution. The first field of view may be wider than the second field of view, and the second resolution may be higher than the first resolution. The step of passing light from the light source through the set of optical components at the first field of view with the first resolution may comprise passing light emitted from the light source through an afocal zoom telescope.

In some embodiments, a method of performing ophthalmic optical coherence tomography with multiple resolutions may be performed using one or more of the systems described herein.

BRIEF DESCRIPTION OF THE DRAWINGS

The accompanying drawings illustrate implementations of the systems and methods disclosed herein and, together with the description, serve to explain the principles of the present disclosure.

FIGS. 2A and 2B show another example embodiment of a system for performing ophthalmic optical coherence tomography with multiple resolutions.

FIGS. 3A and 3B show another example embodiment of a system for performing ophthalmic optical coherence tomography with multiple resolutions.

FIGS. 4A and 4B show another example embodiment of a system for performing ophthalmic optical coherence tomography with multiple resolutions.

FIGS. 5A and 5B show another example embodiment of a system for performing ophthalmic optical coherence tomography with multiple resolutions.

FIGS. 6A and 6B show another example embodiment of a system for performing ophthalmic optical coherence tomography with multiple resolutions.

FIGS. 7A and 7B show another example embodiment of a system for performing ophthalmic optical coherence tomography with multiple resolutions.

Figure 1A:
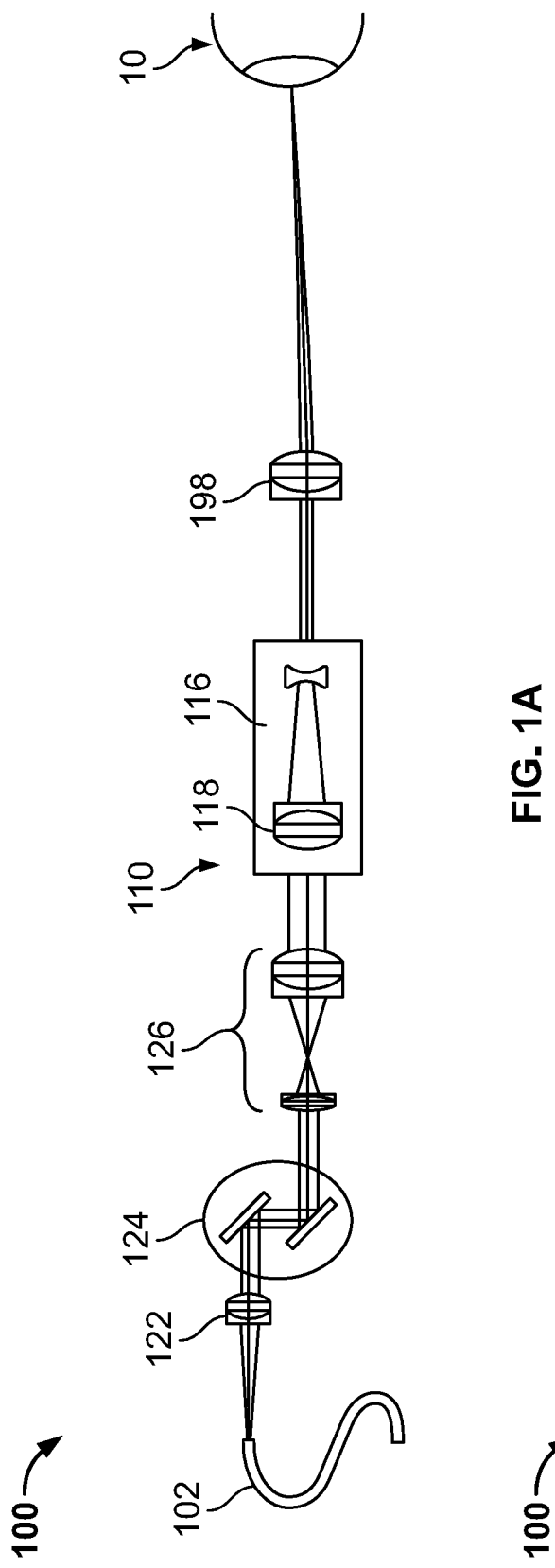
FIGS. 1A and 1B show an example embodiment of a system for performing ophthalmic optical coherence tomography with multiple resolutions.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe the same. It will nevertheless be understood that no limitation of the scope of the disclosure is intended. Any alterations and further modifications to the described systems, devices, instruments, methods, and any further application of the principles of the present disclosure are fully contemplated as would normally occur to one skilled in the art to which the disclosure relates. In particular, the features, components, and/or steps described with respect to one implementation may be combined with the features, components, and/or steps described with respect to other implementations of the disclosure. For simplicity, in some instances the same reference numbers are used throughout the drawings to refer to the same or like parts.

The example embodiments illustrated in FIG. 1A through FIG. 9 are examples of systems for performing ophthalmic optical coherence tomography with multiple resolutions. The systems direct light at an eye 10 for performing OCT of tissue to be examined. The OCT may be performed for posterior segment imaging, for example to examine the retina, and/or for anterior segment imaging, for example to examine the lens and/or cornea.

In each of the embodiments illustrated in FIG. 1A through FIG. 9, the system is adapted to provide imaging at a plurality of fields of view, each with a different resolution. Each of these illustrated systems is adapted to provide imaging both at a first relatively larger or wider field of view with a first relatively lower resolution and at a second relatively smaller or narrower field of view with a second relatively higher resolution.

Figure 1B:
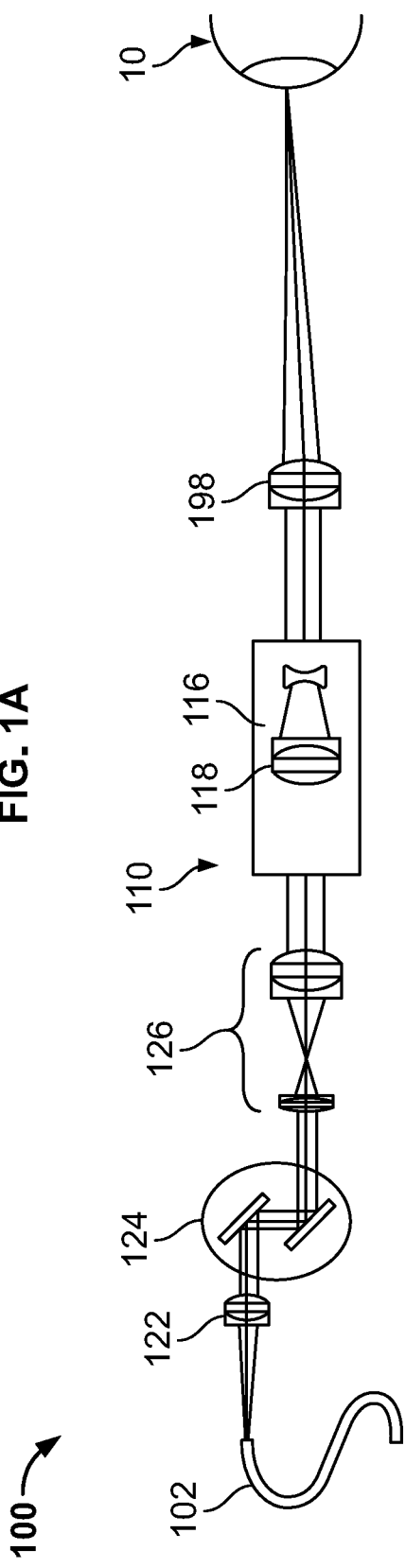

FIGS. 1A and 1B show an example embodiment of a system 100 for performing ophthalmic OCT with multiple resolutions. The system 100 comprises a light source 102, an output lens 198, and a set of optical components 110 between the light source 102 and the output lens 198. The system 100 may comprise a collimating lens 122, two-dimensional (2D) scanner 124, and beam expander 126 as shown. The light source 102 may be a suitable optical fiber. The set of optical components 110 comprises an afocal zoom telescope 116. The set of optical components 110 is adapted to provide imaging both at a first larger field of view with a first lower resolution, as shown in FIG. 1A, and at a second smaller field of view with a second higher resolution, as shown in FIG. 1B.

In the example of FIGS. 1A and 1B, the set of optical components 110 has a first configuration, shown in FIG. 1A, providing the first field of view with the first resolution, and a second configuration, shown in FIG. 1B, providing the second field of view with the second resolution. The afocal zoom telescope 116 comprises a zoom lens 118, wherein the position of the zoom lens 118 is movable between a first position and a second position. When the zoom lens 118 is in its first position, the set of optical components 110 is in its first configuration, and when the zoom lens 118 is in its second position the set of optical components 110 is in its second configuration.

The zoom lens 118 may be under electronic control, enabling the operator to transition between the first configuration and the second configuration rapidly and efficiently. The movement of the zoom lens 118 occurs without having to reposition the system 100 with respect to the patient.

FIGS. 2A and 2B show another example embodiment of a system 200 for performing ophthalmic OCT with multiple resolutions. The system 200 comprises a light source 202, an output lens 298, and a set of optical components 210 between the light source 202 and the output lens 298. The system 200 may comprise a collimating lens 222, two-dimensional (2D) scanner 224, and beam expander 226 as shown. The light source 202 may be a suitable optical fiber. The set of optical components 210 comprises an afocal zoom telescope 216. The set of optical components 210 is adapted to provide imaging both at a first larger field of view with a first lower resolution, as shown in FIG. 2A, and at a second smaller field of view with a second higher resolution, as shown in FIG. 2B.

In the example of FIGS. 2A and 2B, the set of optical components 210 has a first configuration, shown in FIG. 2A, providing the first field of view with the first resolution, and a second configuration, shown in FIG. 2B, providing the second field of view with the second resolution. In this example embodiment, the afocal zoom telescope 216 is movable between a first position as in FIG. 2A and a second position as in FIG. 2B. When the afocal zoom telescope 216 is in its first position as in FIG. 2A, the set of optical components 210 is in its first configuration. When the afocal zoom telescope 216 is in its second position as in FIG. 2B, the set of optical components 210 is in its second configuration. When the afocal zoom telescope 216 is in its first position as in FIG. 2A, the system 200 is configured such that light emitted from the light source 202 passes through the afocal zoom telescope 216, providing the relatively larger field of view. When the afocal zoom telescope 216 is in its second position as in FIG. 2B, the system 200 is configured such that light emitted from the light source 202 does not pass through the afocal zoom telescope 216, providing the relatively higher resolution.

The afocal zoom telescope 216 may be movable between its first position and its second position in any suitable manner. For example, the afocal zoom telescope 216 may be movable between its first position and its second position by rotation of the afocal zoom telescope 216 and/or by translation of the afocal zoom telescope 216. The afocal zoom telescope 216 may be under electronic control, enabling the operator to transition between the first configuration and the second configuration rapidly and efficiently. The movement of the afocal zoom telescope 216 occurs without having to reposition the system 200 with respect to the patient.

FIGS. 3A and 3B show another example embodiment of a system 300 for performing ophthalmic OCT with multiple resolutions. The system 300 comprises a light source 302, an output lens 398, and a set of optical components 310 between the light source 302 and the output lens 398. The system 300 may comprise a collimating lens 322, two-dimensional (2D) scanner 324, and beam expander 326 as shown. The light source 302 may be a suitable optical fiber. The set of optical components 310 comprises an afocal zoom telescope 316. The set of optical components 310 is adapted to provide imaging both at a first larger field of view with a first lower resolution, as shown in FIG. 3A, and at a second smaller field of view with a second higher resolution, as shown in FIG. 3B.

In the example of FIGS. 3A and 3B, the set of optical components 310 has a first configuration, shown in FIG. 3A, providing the first field of view with the first resolution, and a second configuration, shown in FIG. 3B, providing the second field of view with the second resolution. When the set of optical components 310 is in its first configuration as shown in FIG. 3A, the system 300 is configured such that light emitted from the light source 302 travels along a first optical path 370. When the set of optical components 310 is in its second configuration as shown in FIG. 3B, the system 300 is configured such that light emitted from the light source 302 travels along a second optical path 380. In this illustrated example, the first optical path 370 passes through the afocal zoom telescope 316, and the second optical path 380 does not pass through the afocal zoom telescope 316.

In alternate embodiments to examples illustrated herein, the second optical path passes through the afocal zoom telescope, and the first optical path does not pass through the afocal zoom telescope. In other alternate embodiments to examples illustrated herein, both the first optical path and the second optical path pass through one or more afocal zoom telescopes.

In the example of FIGS. 3A and 3B, the set of optical components 310 further comprises a first mirror 330 at an input end 312 of the set of optical components 310. The first mirror 330 is movable between a first position as shown in FIG. 3A and a second position as shown in FIG. 3B. When the first mirror 330 is in its first position as shown in FIG. 3A, the system 300 is configured such that light emitted from the light source 302 travels along the first optical path 370. When the first mirror 330 is in its second position as shown in FIG. 3B, the system 300 is configured such that light emitted from the light source 302 travels along the second optical path 380.

In the example illustrated in FIGS. 3A and 3B, the first position of the first mirror 330 is one in which the first mirror 330 is out of the path of light emitted from the light source 302, thereby allowing light emitted from the light source 302 to travel along the first optical path 370, and the second position of the first mirror 330 is one in which the first mirror 330 is interposed in the path of light emitted from the light source 302, thereby redirecting light emitted from the light source 302 to travel along the second optical path 380. In alternative embodiments, the first position of the first mirror may be one in which the first mirror is interposed in the path of light emitted from the light source, thereby redirecting light emitted from the light source, and the second position of the first mirror may be one in which the first mirror is out of the path of light emitted from the light source, thereby not redirecting light emitted from the light source.

In FIGS. 3A and 3B, in the path of light redirected by the first mirror 330, the system 300 further comprises additional mirrors 332, 334 for redirecting the light back toward a beam splitter 350 located at an output end 314 of the set of optical components 310. The beam splitter 350 allows light from the first optical path 370 to pass through toward the output lens 398, and the beam splitter 350 reflects light from the second optical path 380 toward the output lens 398. In this way, the beam splitter 350 is in both the first optical path 370 and the second optical path 380.

The system 300 further comprises compensation optics 360 in the path of light redirected by the first mirror 330. The compensation optics 360 compensate for the redirection of the beam path.

The first mirror 330 may be under electronic control, enabling the operator to transition between the first configuration and the second configuration rapidly and efficiently. The movement of the first mirror 330 occurs without having to reposition the system 300 with respect to the patient.

FIGS. 4A and 4B show another example embodiment of a system 400 for performing ophthalmic OCT with multiple resolutions. The system 400 comprises a light source 402, an output lens 498, and a set of optical components 410 between the light source 402 and the output lens 498. The system 400 may comprise a collimating lens 422, two-dimensional (2D) scanner 424, and beam expander 426 as shown. The light source 402 may be a suitable optical fiber. The set of optical components 410 comprises an afocal zoom telescope 416. The set of optical components 410 is adapted to provide imaging both at a first larger field of view with a first lower resolution, as shown in FIG. 4A, and at a second smaller field of view with a second higher resolution, as shown in FIG. 4B.

In the example of FIGS. 4A and 4B, the set of optical components 410 has a first configuration, shown in FIG. 4A, providing the first field of view with the first resolution, and a second configuration, shown in FIG. 4B, providing the second field of view with the second resolution. When the set of optical components 410 is in its first configuration as shown in FIG. 4A, the system 400 is configured such that light emitted from the light source 402 travels along a first optical path 470. When the set of optical components 410 is in its second configuration as shown in FIG. 4B, the system 400 is configured such that light emitted from the light source 402 travels along a second optical path 480. In this illustrated example, the first optical path 470 passes through the afocal zoom telescope 416, and the second optical path 480 does not pass through the afocal zoom telescope 416. As described above, alternative configurations are possible, for example in which the second optical path passes through the afocal zoom telescope and the first optical path does not pass through the afocal zoom telescope or in which both the first optical path and the second optical path pass through one or more afocal zoom telescopes.

Similar to the example of FIGS. 3A and 3B, in the example of FIGS. 4A and 4B, the set of optical components 410 further comprises a first mirror 430 at an input end 412 of the set of optical components 410. The first mirror 430 is movable between a first position as shown in FIG. 4A and a second position as shown in FIG. 4B. When the first mirror 430 is in its first position as shown in FIG. 4A, the system 400 is configured such that light emitted from the light source 402 travels along the first optical path 470. When the first mirror 430 is in its second position as shown in FIG. 4B, the system 400 is configured such that light emitted from the light source 402 travels along the second optical path 480.

In the example illustrated in FIGS. 4A and 4B, the first position of the first mirror 430 is one in which the first mirror 430 is out of the path of light emitted from the light source 402, thereby allowing light emitted from the light source 402 to travel along the first optical path 470, and the second position of the first mirror 430 is one in which the first mirror 430 is interposed in the path of light emitted from the light source 402, thereby redirecting light emitted from the light source 402 to travel along the second optical path 480. In alternative embodiments, the first position of the first mirror may be one in which the first mirror is interposed in the path of light emitted from the light source, thereby redirecting light emitted from the light source, and the second position of the first mirror may be one in which the first mirror is out of the path of light emitted from the light source, thereby not redirecting light emitted from the light source.

In FIGS. 4A and 4B, in the path of light redirected by the first mirror 430, the system 400 further comprises additional mirrors 432, 434 for redirecting the light back toward a beam splitter 450 located at an output end 414 of the set of optical components 410. The system 400 further comprises compensation optics 460 in the path of light redirected by the first mirror 430. The compensation optics 460 compensate for the redirection of the beam path.

In the example of FIGS. 4A and 4B, the set of optical components 410 further comprises polarization optics 428 at the input end 412 of the set of optical components 410, prior to the first mirror 430. The polarization optics 428 is adapted to polarize (actively or passively) the beam prior to the first mirror 430. The set of optical components 410 further comprises a polarization rotation device such as a half-wave plate 482 in the second optical path 480, prior to the beam splitter 450 at the output end 414 of the set of optical components 410. The beam splitter 450 is a polarizing beam splitter that directs light at a first polarization through the first optical path 470 and reflects light at a second polarization through the second optical path 480. In this manner, the total power throughput may be optimized.

The first mirror 430 may be under electronic control, enabling the operator to transition between the first configuration and the second configuration rapidly and efficiently. The movement of the first mirror 430 occurs without having to reposition the system 400 with respect to the patient.

FIGS. 5A and 5B show another example embodiment of a system 500 for performing ophthalmic OCT with multiple resolutions. The system 500 is similar to the system 300 shown in FIGS. 3A and 3B, except that system 500 has a second mirror 550 instead of the beam splitter 350 at an output end 514 of the set of optical components. The system 500 comprises a light source 502, an output lens 598, and a set of optical components 510 between the light source 502 and the output lens 598. The system 500 may comprise a collimating lens 522, two-dimensional (2D) scanner 524, and beam expander 526 as shown. The light source 502 may be a suitable optical fiber. The set of optical components 510 comprises an afocal zoom telescope 516. The set of optical components 510 is adapted to provide imaging both at a first larger field of view with a first lower resolution, as shown in FIG. 5A, and at a second smaller field of view with a second higher resolution, as shown in FIG. 5B.

In the example of FIGS. 5A and 5B, the set of optical components 510 has a first configuration, shown in FIG. 5A, providing the first field of view with the first resolution, and a second configuration, shown in FIG. 5B, providing the second field of view with the second resolution. When the set of optical components 510 is in its first configuration as shown in FIG. 5A, the system 500 is configured such that light emitted from the light source 502 travels along a first optical path 570. When the set of optical components 510 is in its second configuration as shown in FIG. 5B, the system 500 is configured such that light emitted from the light source 502 travels along a second optical path 580. In this illustrated example, the first optical path 570 passes through the afocal zoom telescope 516, and the second optical path 580 does not pass through the afocal zoom telescope 516. As described above, alternative configurations are possible, for example in which the second optical path passes through the afocal zoom telescope and the first optical path does not pass through the afocal zoom telescope or in which both the first optical path and the second optical path pass through one or more afocal zoom telescopes.

Similar to the example of FIGS. 3A and 3B, in the example of FIGS. 5A and 5B, the set of optical components 510 further comprises a first mirror 530 at an input end 512 of the set of optical components 510. The first mirror 530 is movable between a first position as shown in FIG. 5A and a second position as shown in FIG. 5B. When the first mirror 530 is in its first position as shown in FIG. 5A, the system 500 is configured such that light emitted from the light source 502 travels along the first optical path 570. When the first mirror 530 is in its second position as shown in FIG. 5B, the system 500 is configured such that light emitted from the light source 502 travels along the second optical path 580.

In FIGS. 5A and 5B, in the path of light redirected by the first mirror 530, the system 500 further comprises additional mirrors 532, 534 for redirecting the light back toward a second mirror 550 located at an output end 514 of the set of optical components 510. The system 500 further comprises compensation optics 560 in the path of light redirected by the first mirror 530. The compensation optics 560 compensate for the redirection of the beam path.

Like the first mirror 530, the second mirror 550 is movable between a first position as shown in FIG. 5A and a second position as shown in FIG. 5B. When the first mirror 530 is in its first position as shown in FIG. 5A, the second mirror 550 is also in its first position, and the system 500 is configured such that light emitted from the light source 502 travels along the first optical path 570. When the first mirror 530 is in its second position as shown in FIG. 5B, the second mirror 550 is also in its second position, and the system 500 is configured such that light emitted from the light source 502 travels along the second optical path 580.

In the example illustrated in FIGS. 5A and 5B, the first positions of the first mirror 530 and the second mirror 550 are positions in which the first mirror 530 and the second mirror 550 are out of the path of light emitted from the light source 502, thereby allowing light emitted from the light source 502 to travel along the first optical path 570, and the second positions of the first mirror 530 and the second mirror 550 are positions in which the first mirror 530 and the second mirror 550 are interposed in the path of light emitted from the light source 502, thereby redirecting light emitted from the light source 502 to travel along the second optical path 580. In alternative embodiments, the first positions of the first and second mirrors may be ones in which the first and second mirrors are interposed in the path of light emitted from the light source, thereby redirecting light emitted from the light source, and the second positions of the first and second mirrors may be ones in which the first and second mirrors are out of the path of light emitted from the light source, thereby not redirecting light emitted from the light source. In alternative embodiments, in the first positions, a first mirror may be in the light path while a second mirror is out of the light path, while in the second positions, the first mirror may be out of the light path while the second mirror is in the light path.

The first mirror 530 and the second mirror 550 may be under electronic control, enabling the operator to transition between the first configuration and the second configuration rapidly and efficiently. The movement of the first mirror 530 and the second mirror 550 occurs without having to reposition the system 500 with respect to the patient.

FIGS. 6A and 6B show another example embodiment of a system 600 for performing ophthalmic OCT with multiple resolutions. The system 600 comprises a light source 602, an output lens 698, and a set of optical components 610 between the light source 602 and the output lens 698. The system 600 may comprise a collimating lens 622, two-dimensional (2D) scanner 624, and beam expander 626 as shown. The light source 602 may be a suitable optical fiber. The set of optical components 610 comprises an afocal zoom telescope 616. The set of optical components 610 is adapted to provide imaging both at a first larger field of view with a first lower resolution, as shown in FIG. 6A, and at a second smaller field of view with a second higher resolution, as shown in FIG. 6B.

In the example of FIGS. 6A and 6B, the set of optical components 610 has a first configuration, shown in FIG. 6A, providing the first field of view with the first resolution, and a second configuration, shown in FIG. 6B, providing the second field of view with the second resolution. When the set of optical components 610 is in its first configuration as shown in FIG. 6A, the system 600 is configured such that light emitted from the light source 602 travels along a first optical path 670. When the set of optical components 610 is in its second configuration as shown in FIG. 6B, the system 600 is configured such that light emitted from the light source 602 travels along a second optical path 680. In this illustrated example, the first optical path 670 passes through the afocal zoom telescope 616, and the second optical path 680 does not pass through the afocal zoom telescope 616. As described above, alternative configurations are possible, for example in which the second optical path passes through the afocal zoom telescope and the first optical path does not pass through the afocal zoom telescope or in which both the first optical path and the second optical path pass through one or more afocal zoom telescopes.

In the example of FIGS. 6A and 6B, the set of optical components 610 further comprises a first beam splitter 630 at an input end 612 of the set of optical components 610. The first beam splitter 630 splits the incoming beam such that light emitted from the light source 602 travels in the direction of the first optical path 670 and in the direction of the second optical path 680. The set of optical components 610 further comprises a second beam splitter 650 at an output end 614 of the set of optical components 610. The second beam splitter 650 is in both the first optical path 670 and the second optical path 680.

The set of optical components 610 further comprises a first shutter 636 and a second shutter 638 at the input end 612 of the set of optical components 610, positioned after the first beam splitter 630. The first shutter 636 is selectively operable to allow or block light from traveling through the first optical path 670. The second shutter 638 is selectively operable to allow or block light from traveling through the second optical path 680. When the set of optical components 610 is in its first configuration, the second shutter 638 prevents light emitted from the light source 602 from traveling through the second optical path 680, and light emitted from the light source 602 travels through the first optical path 670. When the set of optical components 610 is in its second configuration, the first shutter 636 prevents light emitted from the light source 602 from traveling through the first optical path, and light emitted from the light source 602 travels through the second optical path 680.

In FIGS. 6A and 6B, in the path of light reflected by the first beam splitter 630, the system 600 further comprises mirrors 632, 634 for redirecting the light back toward the second beam splitter 650 located at the output end 614 of the set of optical components 610. The system 600 further comprises compensation optics 660 in the path of light reflected by the first beam splitter 630. The compensation optics 660 compensate for the redirection of the beam path.

The first shutter 636 and the second shutter 638 may be under electronic control, enabling the operator to transition between the first configuration and the second configuration rapidly and efficiently. The movement of the first shutter 636 and the second shutter 638 occurs without having to reposition the system 600 with respect to the patient.

FIGS. 7A and 7B show another example embodiment of a system 700 for performing ophthalmic OCT with multiple resolutions. The system 700 comprises a light source 702, an output lens 798, and a set of optical components 710 between the light source 702 and the output lens 798. The system 700 may comprise a collimating lens 722, two-dimensional (2D) scanner 724, and beam expander 726 as shown. The light source 702 may be a suitable optical fiber. The set of optical components 710 comprises an afocal zoom telescope 716. The set of optical components 710 is adapted to provide imaging both at a first larger field of view with a first lower resolution, as shown in FIG. 7A, and at a second smaller field of view with a second higher resolution, as shown in FIG. 7B.

In the example of FIGS. 7A and 7B, the set of optical components 710 has a first configuration, shown in FIG. 7A, providing the first field of view with the first resolution, and a second configuration, shown in FIG. 7B, providing the second field of view with the second resolution. When the set of optical components 710 is in its first configuration as shown in FIG. 7A, the system 700 is configured such that light emitted from the light source 702 travels along a first optical path 770. When the set of optical components 710 is in its second configuration as shown in FIG. 7B, the system 700 is configured such that light emitted from the light source 702 travels along a second optical path 780. In this illustrated example, the first optical path 770 passes through the afocal zoom telescope 716, and the second optical path 780 does not pass through the afocal zoom telescope 716. As described above, alternative configurations are possible, for example in which the second optical path passes through the afocal zoom telescope and the first optical path does not pass through the afocal zoom telescope or in which both the first optical path and the second optical path pass through one or more afocal zoom telescopes.

In the example of FIGS. 7A and 7B, the set of optical components 710 further comprises polarization optics 736 and a polarization rotation device such as a half-wave plate 738 at the input end 712 of the set of optical components 710. The polarization optics 736 is adapted to polarize (actively or passively) the beam prior to the polarization rotation device 738 and a polarizing beam splitter 730. As an alternative to the polarization optics 736, a light source emitting polarized light may be used. The polarization rotation device 738 is adapted to move between two positions, one in which the polarization of incoming light is rotated and one in which the polarization of incoming light is not rotated (or is rotated by a different amount). The polarizing beam splitter 730 directs light at a first polarization through the first optical path 770 and reflects light at a second polarization through the second optical path 780. The set of optical components 710 further comprises a second polarizing beam splitter 750 at an output end 714 of the set of optical components 710. The second polarizing beam splitter 750 is in both the first optical path 770 and the second optical path 780. In this manner, the total power throughput may be optimized.

In FIGS. 7A and 7B, in the path of light reflected by the first beam splitter 730, the system 700 further comprises mirrors 732, 734 for redirecting the light back toward the second beam splitter 750 located at the output end 714 of the set of optical components 710. The system 700 further comprises compensation optics 760 in the path of light reflected by the first beam splitter 730. The compensation optics 760 compensate for the redirection of the beam path.

The polarization rotation device 738 may be moved between positions in any suitable manner. For example, it may be rotated from a first position, as shown in FIG. 7A, in which the polarization of incoming light is not rotated and therefore permitted by the first beam splitter 730 to travel through the first optical path 770, and a second position, as shown in FIG. 7B, in which the polarization of incoming light is rotated and therefore reflected by the first beam splitter 730 to travel through the second optical path 780. The polarization rotation device 738 may be rotated by any suitable angle. Alternatively, the polarization rotation device 738 may be moved by translation between a position in the light path and a position out of the light path.

The polarization rotation device 738 may be under electronic control, enabling the operator to transition between the first configuration and the second configuration rapidly and efficiently. The movement of the polarization rotation device 738 occurs without having to reposition the system 700 with respect to the patient.

Figure 8:
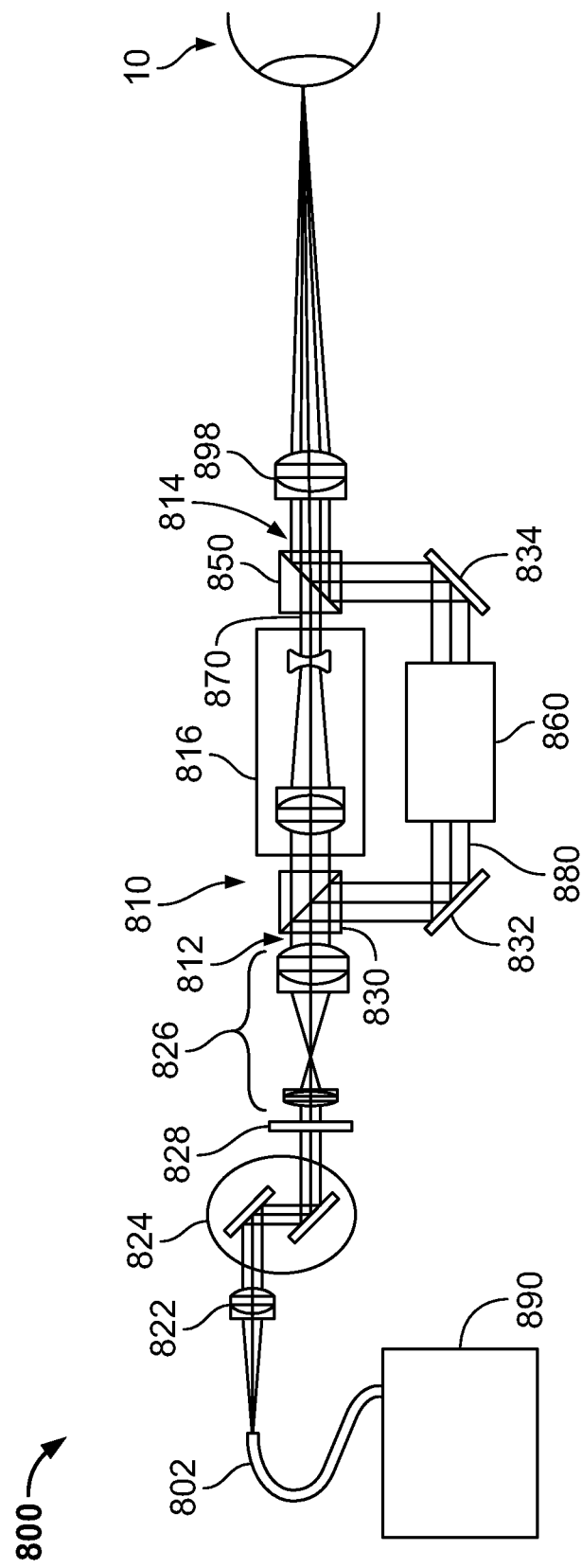
FIG. 8 shows another example embodiment of a system for performing ophthalmic optical coherence tomography with multiple resolutions.

FIG. 8 shows another example embodiment of a system 800 for performing ophthalmic OCT with multiple resolutions. The system 800 comprises a light source 802, an output lens 898, and a set of optical components 810 between the light source 802 and the output lens 898. The system 800 may comprise a collimating lens 822, two-dimensional (2D) scanner 824, and beam expander 826 as shown. The light source 802 may be a suitable optical fiber. The set of optical components 810 comprises an afocal zoom telescope 816. The set of optical components 810 is adapted to provide imaging both at a first larger field of view with a first lower resolution and at a second smaller field of view with a second higher resolution.

In the example of FIG. 8, the set of optical components 810 further comprises a polarization device 828 and an input polarizing beam splitter 830 at an input end 812 of the set of optical components 810. The polarization device 828 polarizes, actively or passively, the light into a plurality of polarizations, for example allowing both TE and TM polarization. The input polarizing beam splitter 830 is adapted to split incoming light such that light at a first polarization travels along a first optical path 870 that passes through the afocal zoom telescope 816 and such that light at a second polarization travels along a second optical path 880 that does not pass through the afocal zoom telescope. The first polarization may be one of TE or TM polarization and the second polarization may be the other of TE or TM polarization. The set of optical components 810 further comprises an output polarizing beam splitter 850 at an output end 814 of the set of optical components 810. The output polarizing beam splitter 850 is in both the first optical path 870 and the second optical path 880. As shown in FIG. 8, the system 800 further comprises an interferometer 890 with detectors adapted to select each of the first polarization and the second polarization.

In FIG. 8, in the path of light reflected by the first beam splitter 830, the system 800 further comprises mirrors 832, 834 for redirecting the light back toward the second beam splitter 850 located at the output end 814 of the set of optical components 810. The system 800 further comprises compensation optics 860 in the path of light reflected by the first beam splitter 830. The compensation optics 860 compensate for the redirection of the beam path.

The system 800 of FIG. 8 allows OCT scanning simultaneously both at a larger field of view with lower resolution and at a smaller field of view with a higher resolution. The detectors in the interferometer 890 select the distinct polarizations in order to process the different fields of view and resolutions.

Figure 9:
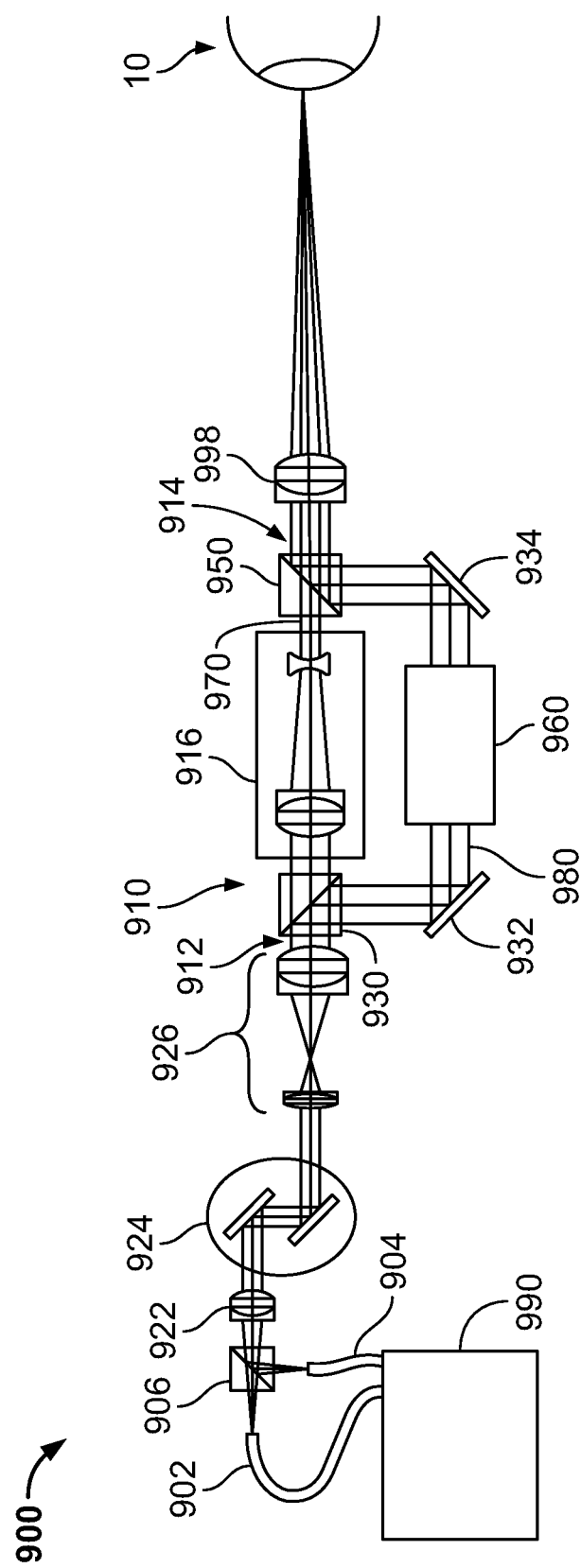
FIG. 9 shows another example embodiment of a system for performing ophthalmic optical coherence tomography with multiple resolutions.

FIG. 9 shows another example embodiment of a system 900 for performing ophthalmic OCT with multiple resolutions. The system 900 is similar to the system 800, except that the system 900 does not have the polarization device 828 and instead comprises two light source 902, 904. Light source 902 emits light at a first polarization (e.g., TE or TM polarization), and light source 904 emits light at a second polarization (e.g., the other of TE or TM polarization). The system 900 further comprises an output lens 998, and a set of optical components 910 between the light sources 902, 904 and the output lens 998. The system 900 may comprise a collimating lens 922, two-dimensional (2D) scanner 924, and beam expander 926 as shown. The light sources 902 and 904 may be suitable optical fibers. A beam splitter 906 may be used to bring light from the light sources 902 and 904 into a common path. The set of optical components 910 comprises an afocal zoom telescope 916. The set of optical components 910 is adapted to provide imaging both at a first larger field of view with a first lower resolution and at a second smaller field of view with a second higher resolution.

Like the example of FIG. 8, in the example of FIG. 9 the set of optical components 910 further comprises an input polarizing beam splitter 930 at an input end 912 of the set of optical components 910. The input polarizing beam splitter 930 is adapted to split incoming light such that light at a first polarization travels along a first optical path 970 that passes through the afocal zoom telescope 916 and such that light at a second polarization travels along a second optical path 980 that does not pass through the afocal zoom telescope. The first polarization may be one of TE or TM polarization and the second polarization may be the other of TE or TM polarization. The set of optical components 910 further comprises an output polarizing beam splitter 950 at an output end 914 of the set of optical components 910. The output polarizing beam splitter 950 is in both the first optical path 970 and the second optical path 980. As shown in FIG. 9, the system 900 further comprises an interferometer 990 with detectors adapted to select each of the first polarization and the second polarization.

As in FIG. 8, in FIG. 9 in the path of light reflected by the first beam splitter 930, the system 900 further comprises mirrors 932, 934 for redirecting the light back toward the second beam splitter 950 located at the output end 914 of the set of optical components 910. The system 900 further comprises compensation optics 960 in the path of light reflected by the first beam splitter 930. The compensation optics 960 compensate for the redirection of the beam path.

The system 900 of FIG. 9 allows OCT scanning simultaneously both at a larger field of view with lower resolution and at a smaller field of view with a higher resolution. The detectors in the interferometer 990 select the distinct polarizations in order to process the different fields of view and resolutions.

A method of performing ophthalmic OCT may be performed using one or more of the systems described herein. The method comprises emitting light from one or more light sources, passing light from the light source(s) through a set of optical components at a first field of view with a first resolution, and passing light from the light source through the set of optical components at a second field of view with a second resolution. The first field of view is wider than the second field of view, and the second resolution is higher than the first resolution. The step of passing light from the light source through the set of optical components at the first field of view with the first resolution comprises passing light emitted from the light source through an afocal zoom telescope.

Persons of ordinary skill in the art will appreciate from this disclosure that the disclosure enables a system for providing ophthalmic OCT at multiple resolutions, at least one resolution being a low resolution with a large field of view and at least one resolution being a high resolution with a small field of view. As an example, the low resolution may be a lateral resolution of about 20 µm with a field of view of about +/−10 mm at the corneal plane of the eye, and the high resolution may be a lateral resolution of about 5 µm with a field of view of about +/−4 mm at the corneal plane of the eye. The system may comprise a relatively small beam diameter such that the scanning speed can be high and not unduly influenced by eye motion.

Persons of ordinary skill in the art will appreciate from this disclosure that the disclosure enables a system for providing ophthalmic OCT at multiple resolutions with rapid changing between resolutions. In some embodiments, components are moved rapidly between configurations. Such movement may be electronically controlled and automated. In other embodiments, the system captures both resolutions simultaneously without the need for movement of components. The pertinent optics may be integrated internally into an optics head to maintain cleanliness and alignment and to prevent damage from handling. In some embodiments, the systems described herein may also allow maintaining a relatively long working distance, for example about 100 mm, for patient comfort. In some embodiments, the systems described herein can avoid the need for external devices that are manually inserted and close to the patient eye.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. A system for performing ophthalmic optical coherence tomography, the system comprising:
   a light source;
   an output lens; and
   a set of optical components between the light source and the output lens, the set of optical components comprising an afocal zoom telescope;
   wherein the set of optical components is adapted to provide imaging both at a first field of view with a first resolution and at a second field of view with a second resolution;
   wherein the first field of view is wider than the second field of view and the second resolution is higher than the first resolution;
   wherein the set of optical components has a first configuration providing the first field of view with the first resolution and a second configuration providing the second field of view with the second resolution;
   wherein the afocal zoom telescope is movable between a first position and a second position, wherein when the afocal zoom telescope is in its first position the set of optical components is in its first configuration, and wherein when the afocal zoom telescope is in its second position the set of optical components is in its second configuration;
   wherein when the afocal zoom telescope is in its first position, the system is configured such that light emitted from the light source passes through the afocal zoom telescope, and wherein when the afocal zoom telescope is in its second position, the system is configured such that light emitted from the light source does not pass through the afocal zoom telescope; and
   wherein the set of optical components is adapted to provide imaging at least at the first field of view by passing light emitted from the light source through the afocal zoom telescope.

2. A system for performing ophthalmic optical coherence tomography as in claim 1, wherein the afocal zoom telescope comprises a zoom lens, wherein the position of the zoom lens is movable between a first position and a second position, wherein when the zoom lens is in its first position the set of optical components is in its first configuration, and wherein when the zoom lens is in its second position the set of optical components is in its second configuration.

3. A system for performing ophthalmic optical coherence tomography as in claim 1, wherein the afocal zoom telescope is movable between its first position and its second position by rotation of the afocal zoom telescope.

4. A system for performing ophthalmic optical coherence tomography as in claim 1, wherein the afocal zoom telescope is movable between its first position and its second position by translation of the afocal zoom telescope.

5. A system for performing ophthalmic optical coherence tomography as in claim 1, wherein when the set of optical components is in its first configuration, the system is configured such that light emitted from the light source travels along a first optical path, and wherein when the set of optical components is in its second configuration, the system is configured such that light emitted from the light source travels along a second optical path.

6. A system for performing ophthalmic optical coherence tomography as in claim 5, wherein the first optical path passes through the afocal zoom telescope, and wherein the second optical path does not pass through the afocal zoom telescope.

7. A system for performing ophthalmic optical coherence tomography as in claim 6, wherein the set of optical components further comprises a first mirror at an input end of the set of optical components, wherein the first mirror is movable between a first position and a second position, wherein when the first mirror is in its first position the system is configured such that light emitted from the light source travels along the first optical path, and wherein when the first mirror is in its second position, the system is configured such that light emitted from the light source travels along the second optical path.

8. A system for performing ophthalmic optical coherence tomography as in claim 7, wherein the set of optical components further comprises polarization optics at an input end of the set of optical components, a polarization rotation device in the second optical path, and a polarizing beam splitter at an output end of the set of optical components.

9. A system for performing ophthalmic optical coherence tomography as in claim 7, wherein the set of optical components further comprises a second mirror at an output end of the set of optical components.

10. A system for performing ophthalmic optical coherence tomography as in claim 6, wherein the set of optical components further comprises a beam splitter at an output end of the set of optical components, and wherein the beam splitter is in both the first optical path and the second optical path.

11. A system for performing ophthalmic optical coherence tomography as in claim 6, wherein the set of optical components further comprises a beam splitter, a first shutter, and a second shutter at an input end of the set of optical components, wherein when the set of optical components is in its first configuration, the second shutter prevents light emitted from the light source from traveling through the second optical path, and wherein when the set of optical components is in its second configuration, the first shutter prevents light emitted from the light source from traveling through the first optical path.

12. A system for performing ophthalmic optical coherence tomography as in claim 6, wherein the set of optical components further comprises a polarization rotation device and a polarizing beam splitter an input end of the set of optical components, and a polarizing beam splitter at an output end of the set of optical components.

13. A system for performing ophthalmic optical coherence tomography as in claim 1, wherein the set of optical components further comprises an input polarizing beam splitter at an input end of the set of optical components, wherein the input polarizing beam splitter is adapted to split incoming light such that light at a first polarization travels along a first optical path that passes through the afocal zoom telescope and such that light at a second polarization travels along a second optical path that does not pass through the afocal zoom telescope.

14. A system for performing ophthalmic optical coherence tomography as in claim 13, wherein the first polarization is one of TE or TM polarization and the second polarization is the other of TE or TM polarization.

15. A system for performing ophthalmic optical coherence tomography as in claim 13, wherein the set of optical components further comprises an output polarizing beam splitter at an output end of the set of optical components, and wherein the output polarizing beam splitter is in both the first optical path and the second optical path.

16. A system for performing ophthalmic optical coherence tomography as in claim 13, wherein the system further comprises an interferometer with detectors adapted to select each of the first polarization and the second polarization.

17. A method of performing ophthalmic optical coherence tomography, the method comprising:
   emitting light from a light source;
   passing light from the light source through a set of optical components at a first field of view with a first resolution; and
   passing light from the light source through the set of optical components at a second field of view with a second resolution;
   wherein the first field of view is wider than the second field of view and the second resolution is higher than the first resolution;
   wherein the set of optical components has a first configuration providing the first field of view with the first resolution and a second configuration providing the second field of view with the second resolution;
   wherein the afocal zoom telescope is movable between a first position and a second position, wherein when the afocal zoom telescope is in its first position the set of optical components is in its first configuration, and wherein when the afocal zoom telescope is in its second position the set of optical components is in its second configuration;
   wherein when the afocal zoom telescope is in its first position, the system is configured such that light emitted from the light source passes through the afocal zoom telescope, and wherein when the afocal zoom telescope is in its second position, the system is configured such that light emitted from the light source does not pass through the afocal zoom telescope; and
   wherein the step of passing light from the light source through the set of optical components at the first field of view with the first resolution comprises passing light emitted from the light source through an afocal zoom telescope.

* * * * *